United States Patent [19]
Combey et al.

[11] 3,976,616
[45] Aug. 24, 1976

[54] BIS(PHOSPHATE) PLASTICIZERS AND PLASTICIZED COMPOSITIONS

[75] Inventors: Malcolm Combey, Mellor Stockport; Raymond Nicolson Birrell, Sale, both of England

[73] Assignee: Ciba-Geigy Corporation, Ardsley, N.Y.

[22] Filed: Dec. 24, 1974

[21] Appl. No.: 536,132

Related U.S. Application Data

[62] Division of Ser. No. 369,040, June 11, 1973, Pat. No. 3,869,526.

[30] Foreign Application Priority Data

June 13, 1972 United Kingdom............... 27501

[52] U.S. Cl. ............................................ 260/30.6 R
[51] Int. Cl.² .................... C08K 5/52; C08L 27/06
[58] Field of Search .................. 260/30.6 R, 929

[56] References Cited

UNITED STATES PATENTS

| | | | |
|---|---|---|---|
| 2,782,128 | 2/1957 | Paist et al. .................... | 106/177 |
| 3,099,676 | 7/1963 | Lanham ........................ | 260/30.6 R |
| 3,288,891 | 11/1966 | Elam ........................... | 260/30.6 R |
| 3,639,318 | 2/1972 | Tijunelis et al. .............. | 260/30.6 R |
| 3,801,526 | 4/1974 | Lorning ....................... | 260/30.6 R |
| 3,859,395 | 1/1975 | Terhune et al. ............... | 260/30.6 R |

FOREIGN PATENTS OR APPLICATIONS

| | | |
|---|---|---|
| 699,333 | 12/1964 | Canada |
| 745,161 | 2/1956 | United Kingdom |

*Primary Examiner*—Allan Lieberman
*Attorney, Agent, or Firm*—Luther A. R. Hall

[57] ABSTRACT

Complex phosphates are used as plasticizers for thermoplastic polymers, especially for polyvinyl chloride.

8 Claims, No Drawings

BIS(PHOSPHATE) PLASTICIZERS AND PLASTICIZED COMPOSITIONS

This is a division of application Ser. No. 369,040 filed on June 11, 1973, and now U.S. Pat. No. 3,869,526.

The present invention relates to organic phosphates, more particularly to complex phosphates.

According to the present invention there is provided a compound or mixture of compounds having the formula $$R-O-\underset{\underset{O}{\|}}{\overset{\overset{OR^1}{|}}{P}}-O-R^2-O-\underset{\underset{OR^4}{|}}{\overset{\overset{O}{\|}}{P}}-OR^3 \qquad I$$

wherein the R, $R^1$, $R^3$ and $R^4$ groupings are the same or different and each may be an alkyl radical containing from 1 to 15 carbon atoms, an aryl or alkaryl radical containing from 6 to 15 carbon atoms, such that R, $R^1$, $R^3$ and $R^4$ are not all alkyl radicals nor are they all aryl radicals containing 6 to 8 carbon atoms.

$R^2$ is an aliphatic straight, branched or cyclic organic alkylene residue containing from 2 to 6 carbon atoms or a hydrocarbon ether residue having between 4 and 20 carbon atoms.

Examples of groups R, $R^1$, $R^3$ and $R^4$ are methyl, ethyl, n-propyl, iso-propyl, n-butyl, sec-butyl, n-hexyl, n-octyl, 2-ethylhexyl, n-dodecyl, phenyl, tolyl, xylyl, isopropylphenyl, butylphenyl, di-isopropylphenyl.

Examples of group $R^2$ are ethylene, 1:2 propylene, 1:3 propylene, 1:3 butylene, 1:4 butylene, 2,2′dimethyl-1:3 propylene, hexamethylene, cyclohexylene, 3-oxa-1,5 pentylene, 3,6-dioxa-1,8,octylene, 3,6,9-trioxa-1,11-undecylene.

Examples of products of formula I are given in the following Table 1.

Table 1

| R | $R^1$ | $R^2$ | $R^3$ | $R^4$ |
|---|---|---|---|---|
| Ph— | Ph— | —CH$_2$CH$_2$OCH$_2$CH$_2$— | C$_8$H$_{17}$— | C$_8$H$_{17}$— |
| Ph— | C$_8$H$_{17}$— | —CH$_2$CH$_2$OCH$_2$CH$_2$— | Ph— | C$_8$H$_{17}$— |
| C$_8$H$_{17}$— | Ph— | —CH$_2$CH$_2$OCH$_2$CH$_2$— | C$_8$H$_{17}$— | C$_8$H$_{17}$— |
| Ph— | C$_8$H$_{17}$— | —CH$_2$CH$_2$OCH$_2$CH$_2$— | Ph— | Ph— |
| (iPr)Ph— | (iPr)Ph— | —CH$_2$CH$_2$OCH$_2$CH$_2$— | (iPr)Ph— | (iPr)Ph— |
| (iPr)Ph— | (iPr)Ph— | —CH$_2$CH$_2$OCH$_2$CH$_2$—<br>—CH$_2$CH$_2$O— | (iPr)Ph— | (iPr)Ph— |
| Ph— | C$_6$H$_{13}$— | —CH$_2$CH$_2$— | Ph— | Ph— |
| C$_2$H$_5$ | C$_2$H$_5$— | —CH$_2$CH$_2$CH$_2$— | Ph— | Ph— |
| (C$_4$H$_9$)Ph— | C$_3$H$_7$— | —CH$_2$—C(CH$_3$)$_2$—CH$_2$— | (C$_4$H$_9$)Ph— | C$_3$H$_7$— |
| C$_{12}$H$_{25}$— | Ph— | —(CH$_2$)$_6$— | (nC$_3$H$_7$)Ph— | (nC$_3$H$_7$)Ph— |
| (C$_2$H$_5$)Ph— | CH$_3$— | —Ph— | (C$_2$H$_5$)Ph— | (C$_2$H$_5$)Ph— |

The compounds of the present invention may, if desired, be prepared by the following methods:

1. An aliphatic alcohol or an appropriate phenol or both, or a mixture of one or both of these with phenol is reacted with phosphorus oxychloride and a diol in any order.

2. A triorgano phosphate is transesterified with a diol, polyol or diphenol preferably in the presence of a metallic transesterification catalyst, for instance barium or sodium.

In both these methods, the diol used may be for example ethylene glycol, diethylene glycol, a polyethylene glycol having a molecular weight of approximately 200, tetramethylene glycol or hexamethylene glycol.

In British Pat. No. 1,146,173 there is claimed a process of producing phosphate esters which comprises contacting phenol with an alkylating agent containing from two to sixteen carbon atoms per molecule, and contacting the alkylated phenol product with a phosphorylating agent to producing a triaryl phosphate ester or mixture of two or more such esters, the proportion of alkylating agent being within the range of from 5% to 65% by weight based on the weight of the phenol with which it is contacted.

Preferred compounds of the present invention having the formula I may be prepared a) by reacting an alkyl aryl phosphochloridate with a diol in the presence of a base e.g. pyridine or the alkali metal salt of the diol such as the sodium salt, or b) by reacting the phosphate esters prepared by the process claimed in BP 1,146,173 with a diol or c) reacting an alkylated phenol product obtained in the first stage of the process claimed in claim 1 of British Patent No. 1,146,173 with the product obtained by reacting a diol with phosphorus oxychloride or d) by reacting a mixture of an alcohol with a phenol, or an alkyl phenol or both with the reaction product of phosphorus oxychloride and a diol.

Some of the phosphochloridates are novel and may be prepared as follows:

The alkyl aryl phosphochloridate in method a) may be prepared from a 1:1 molar ratio of phenol and phosphorus oxychloride and afterwards reacting with an alcohol.

Diaryl phosphochloridates may be prepared by reacting 2 molar proportions of phenol with 1 molar proportion of phosphorus oxychloride in the presence of an aluminium chloride catalyst.

Dialkyl phosphochloridates may be prepared by reacting alcohol with phosphorus trichloride to give dialkyl hydrogen phosphite, and then chlorinating the phosphite with chlorine gas.

Examples of compounds of the present invention are those prepared from diethylene glycol and a mixture of phosphate esters which is prepared from an alkylated phenol product in which the proportion of alkylating agent to phenol is from 10% to 40% by weight based on the weight of phenol. Preferred alkylating agents are propylene and isobutylene.

The compounds of the present invention may be used in admixture with ordinary triorgano monophosphates in any proportion.

The compounds of the present invention combine the properties of traditional phosphate plasticisers and those of polymeric plasticisers. While retaining the desirable features of the traditional phosphates such as ease of processing, and self-extinguishing properties, they also have the following advantages, 1. They have better non-migratory characteristics than traditional phosphates;
2. They have lower volatility.
3. They have more resistance to extraction.

The present invention also provides compositions of thermoplastic polymers, especially vinyl chloride polymers and co-polymers, and a plasticing proportion of a phosphate compound of formula I or a mixture of said compounds, preferably in an amount within the range of from 5% to 100% by weight of the polymer, and especially from 30% to 70%.

The following Examples illustrate the invention. Parts and percentages are by weight unless otherwise stated. Parts by weight bear the same relation to parts by volume as do kilograms to liters.

EXAMPLE 1

A mixture of phosphate esters having an average molecular weight of about 400 consisting of triphenyl phosphate and phosphates containing isopropylated phenyl residues, is prepared by phosphorylating an iso-propylated phenol product in which the proportion of iso-propyl group is 30% by weight, based on the weight of phenol.

810 parts of this mixture of phosphate esters were charged into the reaction vessel under an atmosphere of nitrogen: 4 parts of Sodium metal were then added and the temperature raised to 100°C. 106 parts of diethylene glycol were then added over 30 minutes with stirring at 100°C followed by stirring for a further 30 minutes.

After this addition the pressure was reduced to 200 millimeters of mercury and the temperature of the reaction mass was raised to 200°C over 1 hour. As the phenols distilled slowly, the pressure was gradually reduced to 10 millimeters of mercury over 1½ hours and distillation continued for 1 hour until all phenols had been removed.

The reaction mass was cooled to 18°C and dissolved in 500 parts by volume of toluene. This solution was washed once with 500 parts of a 5% solution of sodium hydroxide and twice with 500 parts of a 5% sodium sulphate solution. After the aqueous layer had been separated the toluene solution was evaporated to dryness to give 450 parts of a yellow mobile liquid which is a mixture containing triarylphosphates, and complex phosphates of formula I.

The refractive index at 25°C was 1.5378.

EXAMPLE 2

A mixture of phosphate esters having an average molecular weight of about 400 consisting of triphenyl phosphate and phosphates containing isopropylated phenyl residues, is prepared by phosphorylating an iso-propylated phenol product in which the proportion of iso-propyl group if 30% by weight, based on the weight of phenol. 4 parts of sodium metal were added in small proportions over 30 minutes to 106 parts of diethylene glycol at 75°C under an atmosphere of nitrogen.

This solution was added over 30 minutes with stirring to 810 parts of the mixture of phosphate esters heated to 100°C followed by stirring for a further 30 minutes.

After this addition the pressure was reduced to 200 millimeters of mercury and the temperature of the reaction mass was raised to 200°C over 1 hour. As the phenols distilled slowly, the pressure was gradually reduced to 10 millimeters of mercury over 1½ hours and distillation continued for 1 hour until all phenols had been removed.

The reaction mass was cooled to 18°C and dissolved in 500 parts by volume of toluene. This solution was washed once with 500 parts of a 5% solution of sodium hydroxide and twice with 500 parts of a 5% sodium sulphate solution. After the aqueous layer had been separated the toluene solution was evaporated to dryness to give 450 parts of a yellow mobile liquid which is a mixture containing triaryl phosphates, and complex phosphates of formula I.

The refractive index at 25°C was 1.5360.

EXAMPLE 3

The phosphate of Example 3 was prepared in the manner described in Example 1 but using triethylene glycol instead of the diethylene glycol there used and contains a compound of formula:

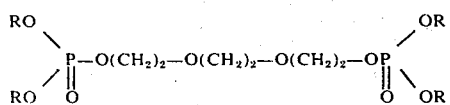

in which the R groupings are a mixture of phenyl and isopropyl phenyl.

EXAMPLE 4

A mixture of 55.7 grams (0.53 moles) of diethylene glycol, 24.2 grams (1.05 moles) sodium and 350 grams toluene was refluxed with stirring under nitrogen for 3 hours. A suspension of the disodium salt of diethylene glycol resulted which was cooled to room temperature. The stirred suspension was then added portionwise over 1 hour to a mixture of 0.5 moles of di-2-ethylhexylphosphochloridate and 0.5 moles of diphenyl phosphochloridate with stirring under nitrogen. The reaction temperature was kept between 0° and 5°C by ice-salt cooling.

When the addition was complete, the reaction mixture was stirred for 1 hour at 0° to 5°C followed by 2 hours at 50°C.

The product was then washed with

1 × 400 milliliters of 5% sodium hydroxide solution and

2 × 400 milliliters of 5% sodium sulphate solution

The organic layer was then evaporated to dryness at 100°C and 1.0 millimeters of mercury pressure to give 290 grams of a mixture containing a compound having the formula

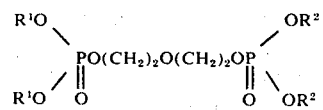

in which $R^1$ is 2-ethylhexyl and $R^2$ is phenyl.

The refractive index at 25°C was 1.4841. The viscosity at 25°C was 125.9 centistokes and the acid and hydroxyl values were 0.08 and 8 milligrams potassium hydroxide per gram respectively.

EXAMPLE 5

A mixture containing a compound having the formula:

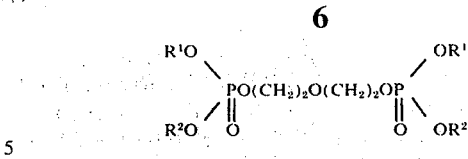

in which $R^1$ is 2-ethylhexyl and $R^2$ is phenyl was prepared in a similar manner to that described in Example 4 except that 1 mole of phenyl-2-ethylhexyl phosphochloridate was used instead of the mixture of 0.5 moles of di-2-ethylhexylphosphochloridate and 0.5 moles of diphenyl phosphochloridate. The yield was 278 grams (91% theory). The refractive index was 1.4674. The viscosity was 78.94 centistokes at 25°C. The acid and hydroxyl values were 0.06 and 16 milligrams potassium hydroxide per gram respectively.

EXAMPLE 6

A mixture containing a compound having the formula

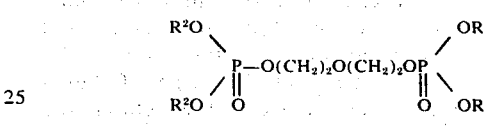

in which $R^1$ is 2-ethyl hexyl and $R^2$ is phenyl was prepared in a similar manner to that described in Example 4 except that 0.5 moles of phenyl-2-ethylhexylphosphochloridate were used instead of the di-2-ethylhexylphosphochloridate. The yield was 300 grams (90% theory). The refractive index was 1.5139. The viscosity was 136.4 centistokes at 25°C. The acid and hydroxyl values were 2.3 and 28 milligrams potassium hydroxide per gram respectively.

EXAMPLE 7

The phosphate of Example 7 was prepared in similar manner to Example 4 but using di-isopropyl phenyl phosphochloridate and diethylene glycol and has the formula:

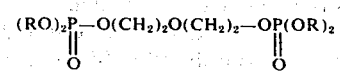

where the R groupings are a mixture of phenyl and isopropyl phenyl.

EXAMPLES 8 to 10

Each of the compounds of Examples 1, 3 and 7 was compounded into PVC using the following formulation:

| | |
|---|---|
| PVC Breon S125/12 | 100 parts by weight |
| Plasticiser | 50 parts by weight |
| White lead paste | 4 parts by weight |
| Calcium stearate | 1 part by weight |

Uniform 0.050 inch thick sheets of PVC were obtained by milling the dry blended components for 15 minutes at 165°C and pressing the hide at 175°C in a plate and frame press.

The migration resistance of the compounds was determined by placing two 2½ inch diameter, 0.050 inch thick PVC discs on either side of an unvulcanised natural rubber disc of the same size and storing the assembly at 70°C for 7 days. After separating the discs, the increase in weight of the rubber was determined. The degree of migration is expressed as the % weight increase in the natural rubber substrate held between the plasticised PVC discs. The plasticisers are compared under conditions of equal compound flexibility as measured by 100% modulus.

The migration resistance of the Compounds of Examples 8, 9 and 10 are given in Table I.

TABLE I

| Examples | Compound of Example | Natural Rubber Migration % |
|---|---|---|
| 8 | 1 | 2.5 |
| 9 | 3 | 5.2 |
| 10 | 7 | 2.4 |

COMPARATIVE EXAMPLE A

The migration resistance of a triarylphosphate mixture prepared by phosphorylating an isopropylated phenol product in which the proportion of isopropyl group is 30% by weight based on the weight of phenol was determined in a similar manner to the method used in Examples 8, 9 and 10. The natural rubber migration was found to be 8.7%. The plasticisers of the present invention as in Examples 8, 9 and 10 show much lower migration into rubber than the triarylphosphate mixture of Comparative Example A.

EXAMPLES 11 to 13

Each of the compounds of Examples 4 to 6 were compounded into PVC using the following formulation:

| PVC Breon S125/12 | 100 parts by weight |
| Plasticiser | 54 parts by weight |
| White lead paste | 4 parts by weight |
| Calcium stearate | 1 part by weight |

Petrol extractions were performed on 0.007 inch film, which was immersed in a mixture of 25 parts toluene and 75 parts iso octane for 1 hour at 23°C. The per cent weight loss from the PVC film was calculated and the results are shown in Table II

TABLE II

| Examples | Compound of Example | Petrol Extraction % |
|---|---|---|
| 11 | 4 | 9.6 |
| 12 | 5 | 11.3 |
| 13 | 6 | 5.2 |

COMPARATIVE EXAMPLE B

The petrol extraction of a product having the formula:

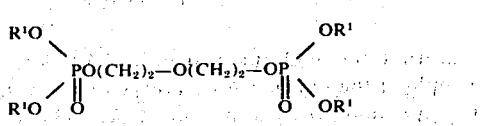

in which $R^1$ is 2-ethylhexyl, prepared from di-2-ethylhexylphosphochloridate and the sodium salt of diethylene glycol, was determined in a similar manner to the method used in Examples 11 to 13. The petrol extraction was found to be 22%, much higher than the products of our invention as in Examples 11 to 13.

EXAMPLE 14

By following a similar procedure to that described in Example 4 but using 18.1 grams of sodium 35.5 grams of neopentyl glycol, 500 grams toluene and 255.4 grams of di-ethylhexylphosphochloridate, 220 grams of a complex phosphate was obtained.

We claim:
1. A composition comprising a vinyl chloride polymer or copolymer and as plasticizer therefor 5 to 100% by weight of the polymer of a bis-phosphate compound of the formula

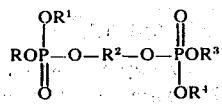

wherein
the R, $R^1$, $R^3$ and $R^4$ groupings are the same or different and each may be an alkyl radical containing from 1 to 15 carbon atoms, phenyl or alkylphenyl radical of 6 to 15 carbon atoms such that R, $R^1$, $R^3$ and $R^4$ are not all alkyl radicals nor are they all phenyl or alkylphenyl containing 6 to 8 carbon atoms, and
$R^2$ is a straight, branched or cyclic alkylene containing from 2 to 6 carbon atoms or a mono-, di- or trioxaalkylene of 4 to 20 carbon atoms, or a mixture of said compounds.

2. A composition according to claim 1 wherein the plasticizer is a bis-phosphate compound wherein
R, $R^1$, $R^3$ and $R^4$ are methyl, ethyl, n-propyl, isopropyl, n-butyl, sec-butyl, n-hexyl, n-octyl, 2-ethylhexyl, n-dodecyl, phenyl, tolyl, xylyl, isopropylphenyl, butylphenyl or diisopropylphenyl, and
$R^2$ is ethylene, 1,2-propylene, 1,3-propylene, 1,3-butylene, 1,4-butylene, 2,2-dimethyl-1,3-propylene, hexamethylene, cyclohexylene, 3-oxa-1,5-pentylene, 3,6-dioxa-1,8-octylene or 3,6,9-trioxa-1,11-undecylene.

3. A composition according to claim 1 wherein the plasticizer is a bis-phosphate compound wherein
R, $R^1$, $R^3$ and $R^4$ are a mixture of phenyl and isopropylphenyl, and
$R^2$ is 3-oxa-1,5-pentylene or 3,6-dioxa-1,8-octylene.

4. A composition according to claim 1 wherein the plasticizer is a bis-phosphate compound wherein
R and $R^1$ are 2-ethylhexyl,
$R^3$ and $R^4$ are phenyl, and
$R^2$ is 3-oxa-1,5-pentylene.

5. A composition according to claim 1 wherein the plasticizer is a bis-phosphate compound wherein
R and $R^3$ are 2-ethylhexyl,
$R^1$ and $R^4$ are phenyl, and
$R^2$ is 3-oxa-1,5-pentylene.

6. A composition according to claim 1 wherein the plasticizer is a bis-phosphate compound wherein
R, $R^1$ and $R^3$ are phenyl,
$R^4$ is 2-ethylhexyl, and
$R^2$ is 3-oxa-1,5-pentylene 7. A composition according to claim 1 wherein the polymer is poly(vinyl chloride).

8. A composition according to claim 1 wherein the plasticizer is present in an amount from 30 to 70% by weight of the polymer.

* * * * *